United States Patent [19]

Neumann

[11] 4,036,976
[45] * July 19, 1977

[54] SUBSTITUTED IMIDAZOLINYLAMINO-INDAZOLES

[75] Inventor: Peter Neumann, Bern, Switzerland

[73] Assignee: Sandoz, Inc., E. Hanover, N.J.

[*] Notice: The portion of the term of this patent subsequent to Nov. 12, 1987, has been disclaimed.

[21] Appl. No.: 617,823

[22] Filed: Sept. 29, 1975

Related U.S. Application Data

[63] Continuation-in-part of Ser. No. 456,521, April 1, 1974, abandoned.

[30] Foreign Application Priority Data

Apr. 5, 1973 Switzerland .................. 4916/73

[51] Int. Cl.² ............. C07D 403/12; A61K 31/415
[52] U.S. Cl. ................... 424/273; 260/309.6; 260/309.7; 260/310 C
[58] Field of Search .............. 260/309.6, 309.7; 424/273

[56] References Cited

U.S. PATENT DOCUMENTS

| | | | |
|---|---|---|---|
| 2,899,426 | 8/1959 | Bloom | 260/309.6 |
| 3,287,469 | 11/1966 | Harvey | 260/309.6 |
| 3,288,805 | 11/1966 | Berg | 260/309.6 |
| 3,359,274 | 12/1967 | Warner | 260/309.6 |
| 3,365,462 | 1/1968 | Holan et al. | 260/309.6 |
| 3,847,934 | 11/1974 | Neumann | 260/309.6 |

FOREIGN PATENT DOCUMENTS

| | | | |
|---|---|---|---|
| 2,258,318 | 6/1973 | Germany | 260/309.6 |
| 599,834 | 3/1948 | United Kingdom | 260/310 C |
| 753,573 | 7/1956 | United Kingdom | 260/310 C |

OTHER PUBLICATIONS

Neumann Chem. Abst. 1973, vol. 79, No. 53324w.
Neumann Chem. Abst. 1975, vol. 82, No. 31323e.

*Primary Examiner*—Natalie Trousof
*Attorney, Agent, or Firm*—Gerald D. Sharkin; Robert S. Honor; Thomas O. McGovern

[57] ABSTRACT

The present invention relates to indazole derivatives of formula

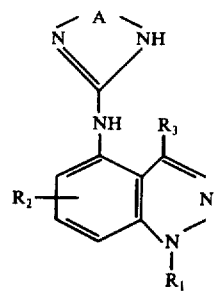

wherein
$R_1$ is hydrogen or alkyl of 1 to 3 carbon atoms,
$R_2$ is hydrogen, halogen, hydroxy, or alkyl, alkoxy or alkylthio of 1 to 3 carbon atoms, and
$R_3$ is hydrogen, halogen, alkyl or alkoxy of 1 to 3 carbon atoms, or hydroxy, and
A is dimethylene or trimethylene, wherein one hydrogen atom may be replaced by hydroxyl or alkyl of 1 to 3 carbon atoms useful as anti hypertensive agents.

29 Claims, No Drawings

SUBSTITUTED IMIDAZOLINYLAMINO-INDAZOLES

This application is a continuation-in-part of my copending application Ser. No. 456,521 filed Apr. 1, 1974 now abandoned the contents of which are incorporated herein by reference.

The present invention relates to new indazole derivatives.

In accordance with the invention there are provided new compounds of formula I,

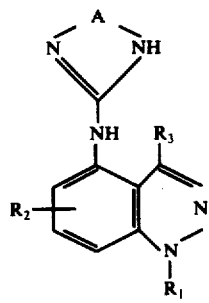

wherein
- $R_1$ is hydrogen or alkyl of 1 to 3 carbon atoms,
- $R_2$ is hydrogen, halogen, hydroxy, or alkyl, alkoxy or alkylthio of 1 to 3 carbon atoms, and
- $R_3$ is hydrogen, halogen, alkyl or alkoxy of 1 to 3 carbon atoms, or hydroxy, and
- A is dimethylene or trimethylene, wherein one hydrogen atom may be replaced by hydroxyl or alkyl of 1 to 3 carbon atoms.

In formula I halogen preferably signifies bromine or especially chlorine. Alkyl may be straight chain or branched alkyl, e.g., methyl, ethyl, or straight chain or branched propyl.

The compounds of formula I are capable of tautomerism. The tautomeric forms are represented by the formulae:

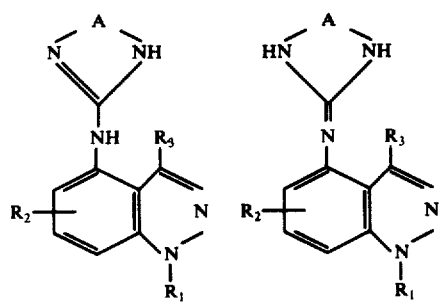

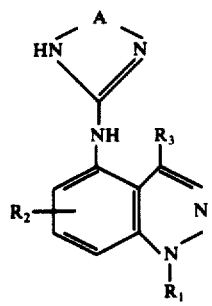

For the sake of simplicity, reference is made hereafter to formula I, or the appropriate corresponding chemical name when referring to the above-mentioned three formulae, but it is not intended that the invention be limited to the compound in the particular form depicted in formula I or defined by a corresponding chemical name. It will be furthermore appreciated that similar tautomerism may exist for structurally analogous compounds described hereinafter and in which case similar considerations apply.

Further, in accordance with the invention a compound of formula I may be obtained by a process comprising a. reacting a compound of formula II,

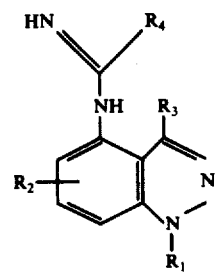

wherein
- $R_1$, $R_2$ and $R_3$ are as defined above, and
- $R_4$ is a reactive group capable of being split off with the hydrogen atom of an amine, with a compound of formula III,

$$NH_2-A-NH_2 \qquad III$$

wherein A is as defined above, or b. subjecting a compound of formula V,

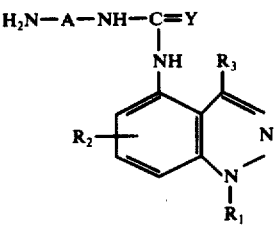

wherein
- $R_1$, $R_2$, $R_3$ and A are as defined above, and
- Y is oxygen or sulphur, to a ring closure, or c. reacting a compound of formula VI,

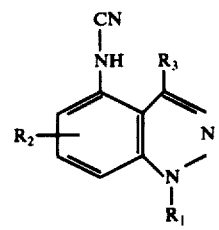

wherein $R_1$, $R_2$ and $R_3$ are as defined above, with a compound of formula III.

The process indicated in section (a) may be effected as described below:

The reactive group $R_4$ capable of being split off preferably signifies a group $-Y-R_5$, $-NH-NO_2$ or $-NH-R_5$, wherein $R_5$ is hydrogen or alkyl of 1 to 3 carbon atoms, and Y is oxygen or sulphur. The reaction is preferably effected in an inert solvent, e.g., water, an alcohol of 1 to 8 carbon atoms such as methanol, or in dioxane, nitromethane or nitrobenzene. A temperature from 50° to 200° C, preferably from 110° to 160° C, is conveniently used. When a salt form of a compound of formula II is used for the reaction, a basic compound of formula III is used as reaction partner and vice versa. When a basic compound of formula III is used, this may replace the solvent. Suitable salt forms of compounds of formulae II and III are the hydrohalic acid salts and p-toluene-sulphonic acid salts. It is convenient to use an excess of a compound of formula III.

The process indicated in section (b) may be effected as described below:

The ring closure of a compound of formula V is conveniently effected in an inert solvent, preferably in an alcohol of 1 to 5 carbon atoms, such as ethanol, or in water or dimethyl formamide. A temperature from 20° to 150° C, preferably from 60° to 110° C, is conveniently used, conveniently a base is present, e.g., an alkali or alkaline earth metal hydroxide such as potassium or sodium hydroxide, or a heavy metal compound, e.g., mercury oxide or lead acetate.

The process indicated in section (c) may be effected as described below:

A compound of formula VI may be reacted with a compound of formula II or a monosalt form thereof, preferably in an inert organic solvent, e.g., an alcohol of 3 to 8 carbon atoms such as n-pentanol. A temperature of 50° to 200° C, preferably of 110° to 160° C, is conveniently used. The reaction is preferably effected in the presence of an excess of a monosalt of a compound of formula III. When a basic compound of formula III is used as reaction partner, this may replace the solvent.

The resulting compounds of formula I may be isolated from the reaction mixture in known manner, e.g., by extraction, precipitation or salt formation, and may be purified in known manner, e.g., by recrystallization.

The compounds of formula II, used as starting materials in the process of section (a), may be produced by a process comprising:

a'. saponifying a compound of formula VIII,

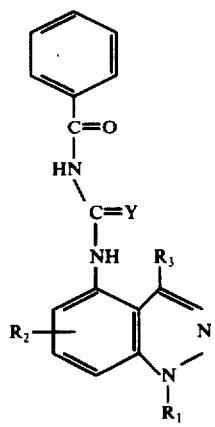

VIII wherein $R_1$ to $R_3$ and Y are as defined above, to produce a compound of formula IIa,

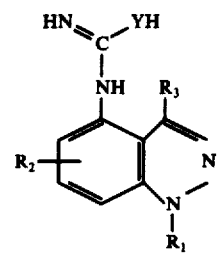

IIa wherein $R_1$ to $R_3$ and Y are as defined above, or b'. alkylating a compound of formula IIa as defined above, to produce a compound of formula IIb,

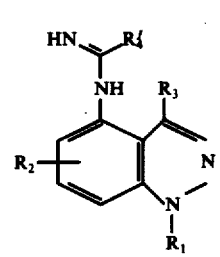

IIb wherein
$R_1$ to $R_3$ are as defined above, and $R_4{}^I$ is $-YAlk$, wherein
Y is as defined above, and
Alk is of 1 to 3 carbon atoms, or
c'. reacting a compound of formula IV,

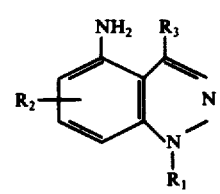

IV wherein $R_1$ to $R_3$ are as defined above, with cyanamide or an alkyl cyanamide, the alkyl radical of which has 1 to 3 carbon atoms, in the presence of an acid, to produce a compound of formula IIc,

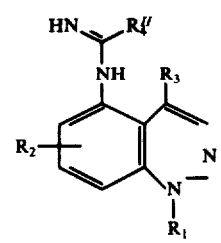

IIc wherein
$R_1$ to $R_3$ are as defined above, and $R_4{}^{II}$ is $-NH-R_5$, wherein
$R_5$ is as defined above, or
d'. reacting a compound of formula IV with methylnitro-nitroguanidine, to produce a compound of formula IId,

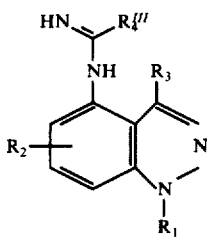

wherein $R_1$ to $R_3$ are as defined above, and $R_4'''$ is —NH—NO$_2$.

Process variant (a') may be effected as follows:

The reaction may be carried out under any conventional alkaline saponification conditions, for example in an aqueous alkali metal hydroxide solution such as sodium hydroxide. The reaction temperature may be the boiling temperature.

A compound of formula VIII may be obtained from a compound of formula IV for example by reacting with the reaction product obtained from benzoyl chloride and ammonium thiocyanate or benzoyl chloride and silver cyanate. The reaction may be effected in an inert solvent such as acetone.

Process variant (b') may be effected under conventional conditions. Preferably the alkylating agent is an alkyl halide of 1 to 3 carbon atoms, especially the iodide or bromide, e.g., methyl iodide or bromide. The reaction is preferably effected in an inert solvent, e.g., methanol. A suitable reaction temperature is the boiling temperature.

Process variant (c') may be effected under conventional conditions in the presence of an acid, e.g., hydrochloric acid. A suitable reaction temperature is from 60° to 140° C. Ethanol may be used as an inert solvent.

Process variant (d') may be effected under conventional conditions for such reactions.

The compounds of formula V, used as starting materials in the process of section (b), may be produced as described below:

A compound of formula IV may be reacted with thiophosgene, preferably in, e.g., 3 N, hydrochloric acid. Preferably room temperature is used. The resulting 4-isothiocyanato-indazole may be allowed to react with a compound of formula III in an inert solvent such as chloroform, conveniently at room temperature.

The compounds of formula VI, used as starting materials in the process of section (c), may be produced as described below:

A compound of formula IIa wherein Y = S, having a tautomeric form of formula:

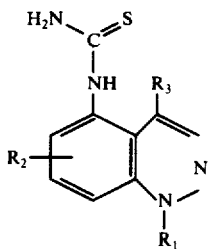

may be dissolved in an aqueous-alkaline medium, e.g., a solution of an alkali metal hydroxide such as potassium hydroxide in water. The solution may then be heated to the boil, and a dehydrosulphurizing agent, e.g., a heavy metal salt such as lead acetate, may be added to the boiling solution.

The compounds of formula IV, used as starting materials in the above process, are known or may be produced in known manner from known starting materials. The compounds of formula III, also used as starting materials, are known.

Insofar as the production of starting materials is not particularly described, these are known or may be produced and purified in accordance with known processes, or in a manner analogous to the processes herein described or to known processes.

Free base forms of the above compounds, e.g., compounds of formulae I and II, may be converted in conventional manner into acid addition salt forms and vice versa.

Suitable inorganic acids for salt formation are: hydrohalic acids, sulphuric and phosphoric acid, and suitable organic acids are: toluenesulphonic, acetic, malonic, succinic, malic, melic and tartaric acid.

In the following non-limitative Examples room temperature (between 20° and 30° C) is used unless otherwise indicated.

EXAMPLE 1:

4-(2-imidazolin-2-ylamino)-1H-indazole [process variant (a)]

17.5 g of S-methyl-N-1H-indazolyl-(4)-isothiuronium iodide are dissolved in 100 cc of methanol, and 4 cc of ethylene diamine are added to the solution. The mixture is heated to the boil at reflux for 1 hour, the solvent is subsequently removed by distillation, and the residue is heated to 150° C for 1 hour. The cooled product is dissolved in 250 cc of 2 N hydrochloric, acid, some active charcoal is added and heating to the boil is effected for a short time. The cooled solution is filtered and the filtrate is made weakly alkaline with 2 N aqueous sodium hydroxide solution. The precipitate is filtered off and washed with water, is then suspended in 150 cc of methanol and heated to the boil. The cooled mixture is filtered. The precipitate is washed with methanol and ether and is 4-(2-imidazolin-2-ylamino)-1H-indazole having an M.P. of 312°-314° C.

The S-methyl-N-1H-indazolyl-(4)-isothiuronium iodide, used as starting material in this Example, is obtained as follows:

9 cc of benzoyl chloride are added to a solution of 8 g of ammonium thiocyanate in 70 cc of acetone in an ice bath, and the mixture is stirred for 10 minutes. A solution of 9 g of 4-amino-indazole in 200 cc of acetone is added, and the resulting mixture is heated to the boil at reflux for 1 hour. The mixture is then concentrated to half its volume and diluted with 500 cc of water. The resulting precipitate is filtered off, added to 250 cc of 2 N aqueous sodium hydroxide solution, the mixture is rapidly brought to the boil and kept at the boil for 5 minutes. The reaction mixture is acidified with glacial acetic acid, the resulting precipitate is filtered after cooling and washed with water. The filter residue is boiled together with 10 g of methyl iodide in 150 cc of absolute methanol for 1 hour and is then evaporated to dryness. Crude S-methyl-N-1H-indazolyl-(4)-isothiuronium iodide is obtained and is used for the above reaction without further purification (M.P. 200°-203° from ethyl acetate/methanol).

EXAMPLE 2

3-chloro-4-(2-imidazolin-2-ylamino)-1H-indazole [process variant (b)]

2.7 g of N-(2-aminoethyl)-N'-(3-chloro-1H-indazolyl-4)thiourea are added to a solution of 0.7 g of potassium hydroxide in 100 cc of methanol, 2.8 g of lead acetate are added, and the resulting mixture is heated to the boil at reflux for 1 hour. The black lead sulphide is then filtered off and the colourless filtrate is concentrated by evaporation. The residue is distributed between water and chloroform. The organic phase is dried and concentrated by evaporation. The residue is crystallized from isopropanol, whereby 3-chloro-4-(2-imidazolin-2-ylamino)-1H-indazole is obtained; the acetate thereof has a M.P. of 245°–250° C.

The N-(2-aminoethyl)-N'-(3-chloro-1H-indazolyl-4)thiourea, used as starting material in this Example, is produced as follows:

8.3 g of 3-chloro-4-nitro-1H-indazole are dissolved in 100 cc of ethyl acetate, 2 g of a 5% palladium/charcoal catalyst are added to the solution, and hydrogenation is effected in a hydrogenating vessel in an atmosphere of hydrogen under normal conditions. After 2 hours the theoretic amount of hydrogen is taken up. The catalyst is filtered off and the solution is concentrated by evaporation. The resulting 4-amino-3-chloro-1H-indazole is sufficiently pure for the next reaction. 4.6 g of this product are dissolved in 160 cc of 3 N hydrochloric acid, and 6 cc of thiophosgene are added to the resulting solution. The resulting emulsion is stirred at room temperature for 15 hours. The resulting light brown precipitate is filtered off and washed thoroughly with water. Purification is effected by taking up the precipitate in 500 cc of ether. The solution is filtered through active charcoal and concentrated by evaporation. The residue is sufficiently pure for the next reaction. After recrystallization from methanol, 3-chloro-4-isothiocyan-1H-indazole, having an M.P. of 216°–220° C, is obtained.

A solution of 5.6 g of 3-chloro-4-isothiocyan-1H-indazole in 200 cc of ether is added dropwise with stirring to a mixture of 5.5 cc of ethylene diamine and 200 cc of ether within 1 hour. The resulting oil is separated from the ether solution and is taken up in 300 cc of methanol. The solution is filtered through active charcoal and concentrated to a small volume (15 cc). The product which crystallizes is drawn off by suction and is washed with ethyl acetate and then with ether. N-(2-amino-ethyl)-N'-(3-chloro-1H-indazolyl-4)thiourea, having an M.P. of 175°–178° C, is obtained.

EXAMPLE 3

4-(2-imidazolin-2-ylamino)-1H-indazole [process variant (c)]

5.7 g of 4-cyanamido-1H-indazole are heated to the boil at reflux for 4 hours, together with 22.5 g of ethylene diamine mono-p-toluene sulphonate in 150 cc of n-pentanol. Cooling is then effected, whereby a crystalline precipitate results. This is filtered off and washed with ethanol. The combined filtrates are concentrated by evaporation, and the resulting residue is distributed between 300 cc of chloroform and 300 cc of aqueous 2 N sodium hydroxide solution. A light beige precipitate is obtained, which is separated and washed with methanol. This precipitate is suspended in 100 cc of methanol and heated to the boil. The resulting mixture is filtered. The residue is washed with methanol and ether and is 4-(2-imidazolin-2-ylamino)-1H-indazole, having an M.P. of 310°–314° C.

The 4-cyanamido-1H-indazole, used as starting material in this Example, is obtained as follows:

8 g of (1H-indazolyl-4)thiourea, having an M.P. of 225°–226° C, are suspended in 75 cc of hot water, and the suspension is converted into a solution by the addition of a solution 25 g of potassium hydroxide in 60 cc of hot water. A boiling hot solution of 19 g of lead acetate in 45 cc of water is rapidly stirred into this solution. A black precipitate is obtained. The mixture is heated to the boil for five minutes, is then cooled in an ice bath and filtered whilst cold. The filtrate is made slightly acid with acetic acid, whereby a white precipitate is obtained, which is filtered off. The residue is dissolved in ethyl acetate, filtered through active charcoal and concentrated by evaporation. The resulting 4-cyanamido-1H-indazole is suffiently pure for the next reaction. After recrystallization from aqueous alcohol, this compound has an M.P. of 218°–220° C.

Using the corresponding starting materials and one of the processes described in Examples 1 to 3, the following compounds of formula I, IIa, IIb, V and VI wherein A is dimethylene are obtained:

| Ex. | $R_1$ | $R_2$ | $R_3$ | M.P. | |
|---|---|---|---|---|---|
| 4 | H | 5-Cl | H | 190–194° | |
| 5 | H | H | Cl | 245–250° | acetate (analogous Example 2) |
| 6 | $CH_3$ | 5-$CH_3$ | H | 173–176° | |
| 7 | $CH_3$ | H | Cl | 253–255° | |
| 8 | H | H | Br | | |
| 9 | H | H | OH | | |
| 10 | $CH_3$ | H | $CH_3O$— | | |
| 11 | $CH_3$ | 5-$CH_3S$— | H | | |
| 12 | H | 6-$CH_3$ | H | 285–288° | |
| 13 | H | 7-$CH_3$ | H | | |
| 14 | H | 6-OH | H | | |
| 15 | $CH_3$ | 6-$CH_3O$— | H | | |
| 16 | $CH_3$ | 6-$CH_3S$— | H | | |
| 17 | $CH_3$ | 5-Cl | H | 145–147° | |
| 18 | H | 5-$CH_3$ | H | 265–270° | (hydrochloride 304–309°) |
| 19 | $CH_3$ | H | H | 228–230° | |
| 20 | H | H | H | 312–314° | (analogous Examples 1 and 3) |

In a manner analogous to that described in Example 1, the following compounds of formula I are obtained, wherein $R_1$ and $R_2$ are hydrogen,

| | $R_3$ | A |
|---|---|---|
| a) | $CH_3$ | —$CH_2$ . $CH_2$ . $CH_2$— |
| b) | H | —$CH(CH_3)$ . $CH_2$ . $CH_2$— |
| c) | H | —$CH_2$ . $CH(OH)$ . $CH_2$— |
| d) | H | —$CH_2$ . $CH(OH)$— | and also the following compounds of formula I wherein

| No. | $R_1$ | $R_2$ | $R_3$ | A |
|---|---|---|---|---|
| 21 | H | H | H | —$CH_2$ . $CH_2$ . $CH_2$— |
| 22 | H | H | H | —$CH_2$ . $CH(CH_3)$— |
| 23 | $CH_3$ | 5-$CH_3$ | H | —$CH_2$ . $CH_2$ . $CH_2$— |
| 24 | $CH_3$ | 5-$CH_3$ | H | —$CH_2$ . $CH(CH_3)$— |
| 25 | $CH_3$ | 5-$CH_3$ | H | —$CH_2$ . $CH(OH)$ . $CH_2$— |
| 26 | H | 5-Cl | H | —$CH_2$ . $CH_2$ . $CH_2$— |
| 27 | H | 6-OH | H | —$CH_2$ . $CH_2$ . $CH_2$— |
| 28 | H | 5-$CH_3O$ | H | —$CH_2$ . $CH_2$ . $CH_2$— |
| 29 | H | 6-$CH_3S$ | H | —$CH_2$ . $CH_2$ . $CH_2$— |
| 30 | H | 7-$CH_3$ | H | —$CH_2$ . $CH_2$ . $CH_2$— |
| 31 | H | H | Cl | —$CH_2$ . $CH_2$ . $CH_2$— |
| 32 | H | H | $CH_3O$ | —$CH_2$ . $CH_2$ . $CH_2$— |
| 33 | H | H | OH | —$CH_2$ . $CH_2$ . $CH_2$— |
| 34 | H | H | $CH_3$ | —$CH_2$ . $CH_2$— |
| 35 | $CH_3$ | 5-$CH_3$ | Cl | —$CH_2$ . $CH_2$— |

The compounds of formula I have not been described in the literature.

The compounds of formula I and IIa–d are useful because they possess pharmacological activity in animals. In particular, the compounds of formulae I and IIa–d are useful as anti-hypertensive agents, as indicated by a lowering of blood pressure of experimentally induced hypertonia in rats on oral administration at a dose of 0.01 to 0,5 mg/kg animal body weight of the compounds. [Method of F. Gross, P. Lustallot and F. Sulser, Arch. exper. Path. Pharmarkol. 229, 381–388 (1956)].

For the above mentioned use the dosage will, of course, vary depending on the compound employed, mode of administration and therapy desired. However, in general, satisfactory results are obtained when administered at a daily dosage of from 0.007 mg to about 0.5 mg per kg animal body weight, conveniently given in divided doses 2 to 4 times a day or in sustained release from. For the larger mammal, the total daily dosage is in the range from about 0.5 to about 30 mg, and dosage forms suitable for oral administration comprise from about 0.1 mg to about 15 mg of the compounds admixed with a solid or liquid pharmaceutical carrier or diluent.

The compounds may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formulae I and Ia–d, in free base form or in pharmaceutically acceptable acid addition salt form, in association with a pharmaceutical carrier or diluent. Such compositions conveniently contain more than 1% by weight of the compound and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan monooleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

An example of a tablet composition comprises 0.2 mg of 4-[2-imidazolin-2-ylamino]-1-methyl-indazole, 1 mg magnesium stearate, 4 mg of polyvinyl pyrrolidone, 5 mg of talc, 10 mg of maize starch, 137.8 mg of lactose, 0.5 mg of dimethyl silicone oil and 1.5 mg of polyethylene glycol 6000.

I claim:

1. A compound of the formula

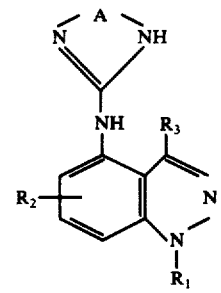

wherein
- $R_1$ is hydrogen or alkyl of 1 to 3 carbon atoms,
- $R_2$ is hydrogen, halogen, hydroxy, or alkyl, alkoxy or alkylthio each of 1 to 3 carbon atoms, and
- $R_3$ is hydrogen, halogen, alkyl or alkoxy each of 1 to 3 carbon atoms, or hydroxy, and
- A is dimethylene, wherein one hydrogen atom may be replaced by hydroxyl or alkyl of 1 to 3 carbon atoms, or a pharmaceutically acceptable acid addition salt thereof.

2. A compound of claim 1 having the formula

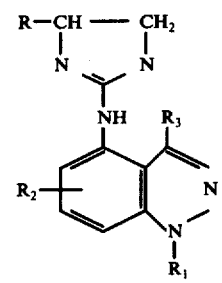

wherein
- $R_1$ is hydrogen or alkyl of 1 to 3 carbon atoms,
- $R_2$ is hydrogen, halogen, hydroxy or alkyl, alkoxy or alkylthio each of 1 to 3 carbon atoms, and
- $R_3$ is hydrogen, halogen, alkyl or alkoxy each of 1 to 3 carbon atoms, or hydroxy, and
- R is hydrogen, hydroxyl or alkyl of 1 to 3 carbon atoms, with the proviso that at least one of $R_1$, $R_2$, $R_3$ and R are other than hydrogen.

3. A compound of claim 1 of the formula

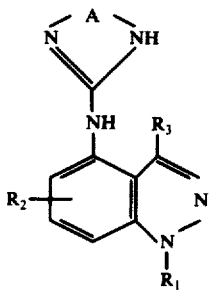

wherein
R₁ is hydrogen or alkyl of 1 to 3 carbon atoms,
R₂ is hydrogen, halogen, hydroxy, or alkyl, alkoxy or alkylthio each of 1 to 3 carbon atoms, and
R₃ is hydrogen, halogen, alkyl or alkoxy each of 1 to 3 carbon atoms, or hydroxy, and
A is dimethylene wherein one hydrogen atom is replaced by hydroxyl or alkyl of 1 to 3 carbon atoms.

4. A compound of claim 1, wherein at least one of R₁, R₂, and R₃ are other than hydrogen.

5. A compound of claim 1, which is 4-(2-imidazolin-2-ylamino)-1H-indazole.

6. A compound of claim 2, which is 3-chloro-4-(2-imidazolin-2-ylamino)-1H-indazole.

7. The compound of claim 1, wherein R₁ is H, R₂ is 5-Cl and R₃ is H and A is dimethylene.

8. The compound of claim 1, wherein R₁ is CH₃, R₂ is 5-CH₃ and R₃ is H and A is dimethylene.

9. The compound of claim 1, wherein R₁ is CH₃, R₂ is H and R₃ is Cl and A is dimethylene.

10. The compound of claim 1, wherein R₁ is H, R₂ is H and R₃ is Br and A is dimethylene.

11. The compound of claim 1, wherein R₁ is H, R₂ is H and R₃ is OH and A is dimethylene.

12. The compound of claim 1, wherein R₁ is CH₃, R₂ is H and R₃ is CH₃O and A is dimethylene.

13. The compound of claim 1, wherein R₁ is CH₃, R₂ is 5-CH₃ and R₃ is H and A is dimethylene.

14. The compound of claim 1, wherein R₁ is H, R₂ is 6-CH₃ is H and A is dimethylene.

15. The compound of claim 1, wherein R₁ is H, R₂ is 7-CH₃ and R₃ is H and A is dimethylene.

16. The compound of claim 1, wherein R₁ is H, R₂ is 6-OH and R₃ is H and A is dimethylene.

17. The compound of claim 1, wherein R₁ is CH₃, R₂ is 6-CH₃O and R₃ is H and A is dimethylene.

18. The compound of claim 1, wherein R₁ is CH₃, R₂ is 6-CH₃S and R₃ is H and A is dimethylene.

19. The compound of claim 1, wherein R₁ is CH₃, R₂ is 5-Cl and R₃ is H and A is dimethylene.

20. The compound of claim 1, wherein R₁ is H, R₂ is 5-CH₃ and R₃ is H and A is dimethylene.

21. The compound of claim 1, wherein R₁ is CH₃, R₂ is H and R₃ is H and A is dimethylene.

22. The compound of claim 1 wherein R₁ is H, R₂ is H, R₃ is H and A is —CH₂CH(OH)—.

23. A pharmaceutical composition useful in treating hypertension comprising a therapeutically effective amount of a compound of claim 1 in association with a pharmaceutical carrier or diluent.

24. A pharmaceutical composition according to claim 23, comprising 0.1 to 15 milligrams per unit dosage.

25. A method of treating hypertension in animals, which comprises administering to an animal in need of such treatment a therapeutically effective amount of a compound of claim 1.

26. A method according to claim 25 in which 0.5 to 30 milligrams of the compound are administered daily.

27. A method according to claim 25 in which 0.1 to 15 milligrams of the compound are administered orally per unit dose.

28. A method according to claim 25 in which the compound is 4-(2-imidazolin-2-ylamino)-1H-imidazole.

29. A method of treating hypertension in animals, which comprises administering to an animal in need of such treatment in therapeutically effective amount of a compound of claim 12.

* * * * *